US008666671B2

(12) United States Patent
Lanzara

(10) Patent No.: US 8,666,671 B2
(45) Date of Patent: Mar. 4, 2014

(54) METHOD FOR DETERMINING DRUG-MOLECULAR COMBINATIONS THAT MODULATE AND ENHANCE THE THERAPEUTIC SAFETY AND EFFICACY OF BIOLOGICAL OR PHARMACEUTICAL DRUGS

(75) Inventor: Richard G. Lanzara, New York, NY (US)

(73) Assignee: Enhanced Pharmaceuticals, Inc., New York, NY (US)

( * ) Notice: Subject to any disclaimer, the term of this patent is extended or adjusted under 35 U.S.C. 154(b) by 1031 days.

(21) Appl. No.: 12/167,751

(22) Filed: Jul. 3, 2008

(65) Prior Publication Data

US 2009/0012717 A1 Jan. 8, 2009

Related U.S. Application Data

(60) Provisional application No. 60/948,108, filed on Jul. 5, 2007.

(51) Int. Cl.
*G06F 19/00* (2011.01)

(52) U.S. Cl.
USPC ........................................................ 702/19

(58) Field of Classification Search
None
See application file for complete search history.

(56) References Cited

U.S. PATENT DOCUMENTS

| | | | |
|---|---|---|---|
| 5,597,699 A | 1/1997 | Lanzara | |
| 6,219,622 B1 | 4/2001 | Schmidt | |
| 6,593,094 B2 | 7/2003 | Lanzara | |
| 6,638,543 B2 * | 10/2003 | Kang et al. | 424/757 |
| 6,673,558 B1 | 1/2004 | Lanzara | |
| 2002/0156043 A1 | 10/2002 | Pfost | |
| 2004/0176315 A1 | 9/2004 | Pfost | |
| 2005/0089890 A1 | 4/2005 | Cubicciotti | |
| 2006/0228694 A1 | 10/2006 | Janoff et al. | |
| 2007/0185145 A1 | 8/2007 | Royds | |
| 2008/0096802 A1 | 4/2008 | Bussolari et al. | |

OTHER PUBLICATIONS

Berg, KA et al. "Effector Pathway-Dependent Relative Efficacy at Serotonin Type 2A and 2C Receptors: Evidence for Agonist-Directed Trafficking of Receptor Stimulus" Molecular Pharmacology, 54:94-104 (1998), 11 pages.
Bond, RA, et al. "Physiological Effect of Inverse Agonists in Transgenic Mice with Myocardial Overexpression of the Beta-2-Adrenoceptor" Letters to Nature, vol. 374:273-276 (1995), 5 pages.
Borisy, AA, et al. "Systematic discovery of multicomponent therapeutics" PNAS vol. 100:7977-7982 (Jun. 2003), 6 pages.
Christopoulos, A et al. "G Protein-Coupled Receptor Allosterism and Complexing" Pharmacological Reviews, vol. 54:323-374 (2002), 52 pages.
Clarke, WP. "What's for Lunch at the Conformational Cafeteria?" Molecular Pharmacology vol. 67:1819-1821 (2005), 3 pages.
Colquhoun, D. "Binding, gating, affinity and efficacy: The interpretation of structure-activity relationships for agonists and of the effects of mutating receptors" British Journal of Pharmacology, 125 923-947 (1998), 25 pages.
Dillon, PF et al. "Antioxidant-independent ascorbate enhancement of catecholamin-induced contractions of vascular smooth muscle" Am J Physiol Hear Circ Physiol 286:H2352-H2360 (2004), 9 pages.
Galandrin, S et al. "Distinct Signaling Profiles of B1 and B2 Adrenergic Receptor Ligands toward Adenylyl Cyclase and Mitogen-Activated Protein Kinase Reveals the Pluridimensionality of Efficacy" Molecular Pharmacology, 70:1575-1584 (2006), 10 pages.
Kenakin, T "Efficacy at G-Protein-Coupled Receptors" Nature Reviews/Drug Discovery, vol. 1:103-110 (2002), 8 pages.
Kenakin, T et al. "The ligand paradox between affinity and efficacy: can you be there and not make a difference?" Trends in Pharmacological Sciences, vol. 23:275-280 (2002), 6 pages.
Kenakin, T. "Drug Efficacy at G Protein-Coupled Receptors" Annu. Rev. Pharmacol. Toxicol., 42:349-379 (2002), 31 pages.
Kenakin, T. "Ligand-selective receptor conformations revisited: the promise and the problem", Trends in Pharmacological Sciences, vol. 24:346-354 (Jul. 2003), 9 pages.
Lane, RJ et al. "Protean Agonism at the Dopamine D2 Receptor: (S)-3(3-Hydroxyphenyl)-N-propylpiperidine Is an Agonist for Activation of Go1 but an Antagonist/Inverse Agonist for Gi1, Gi2, and Gi3" Molecular Pharmacology, vol. 71: 1349-1359 (2007), 11 pages.
Lanzara, RG "A Novel Biophysical Model for Receptor Response" Canadian Journal of Physiology and Pharmacology, 72:559 (1994), 12 pages.
Lanzara, RG "Optimal Agonist/Antagonist Combinations Maintain Receptor Response by Preventing Rapid B1-adrenergic Receptor Desensitization" International Journal of Pharmacology, 1(2):122-131 (2005), 10 pages.
Lanzara, RG "Weber's Law Modeled by the Mathematical Description of a Beam Balance" Mathematical Biosciences, 22:89-94 (1994), 6 pages.

(Continued)

*Primary Examiner* — Lori A Clow
(74) *Attorney, Agent, or Firm* — St. Onge Steward Johnston & Reens LLC

(57) ABSTRACT

A method that creates a new class of pharmaceutical combinations (specific ratio combinations) that offer an improved therapeutic profile with reduced side effects is provided. Safer, more cost-effective drugs for treating various diseases or medical conditions are created by combining receptor activating, inhibiting or modulating drugs in specific ratio combinations that optimize the therapeutic profiles for various pharmaceutical compositions. The method demonstrates how to combine biological or pharmaceutical molecules or drugs in order to create specific ratio combinations that are optimized to improve the overall safety and therapeutic efficacy of the individual molecules or drugs alone. These techniques create novel receptor-activating drugs that are anticipated to prove useful for future therapeutic treatments.

35 Claims, 9 Drawing Sheets

(56) References Cited

OTHER PUBLICATIONS

Lefkowitz, RJ, et al. "Constitutive activity of receptors coupled to guanine nucleotide regulatory proteins" Trends in Pharmacological Sciences, vol. 14: 303-307 (Aug. 1993), 5 pages.

Lehar, J et al. "Chemical combination effects predict connectivity in biological systems" Molecular Systems Biology 3, Article No. 80:1-14 (2007), 14 pages.

Neubig, RR "Missing Links: Mechanisms of Protean Agonism" Molecular Pharmacology, vol. 71:1200-1202 (2007), 3 pages.

Rubenstein, LA et al. "Activation of G protein-coupled receptors entails cysteine modulation of agonist binding" Journal of Molecular Structure (Theochem), 430:57-71 (1998), 15 pages.

Rubenstein, LA et al. "Molecular dynamics of a biophysical model for B2-adrenergic and G protein-coupled receptor activation" Journal of Molecular Graphics and Modelling, 25:396-409 (2006), 15 pages.

Stout, BD et al. "Rapid Desensitization of the Serotonin2c Receptor System: Effector Pathway and Agonist Dependence" The Journal of Pharmacology and Experimental Therapeutics, vol. 302(3):957-62 (2002), 6 pages.

Urban, JD et al. "Functional Selectivity and Classical Concepts of Quantitative Pharmacology" The Journal of Pharmacology and Experimental Therapeutics, 320:1-13 (2007), 13 pages.

Vogel, R, et al "Conformation of the Active and Inactive States of Opsin" The Journal of Biological Chemistry, vol. 276: 38487-38493 (2001), 7 pages.

Wei, H et al. "Independent B-arrestin 2 and G protein-mediated pathways for angiotensin II activation of extracellular signal-regulated kinases 1 and 2" PNAS, vol. 100:10782-10787(Sep. 2003), 6 pages.

* cited by examiner

METHOD FOR DETERMINING DRUG-MOLECULAR COMBINATIONS THAT MODULATE AND ENHANCE THE THERAPEUTIC SAFETY AND EFFICACY OF BIOLOGICAL OR PHARMACEUTICAL DRUGS

RELATED APPLICATIONS

This patent application claims the benefit of, under Title 35, United States Code, Section 119(e), U.S. Provisional Patent Application No. 60/948,108, filed Jul. 5, 2007.

FIELD OF THE INVENTION

The present invention relates generally to drug combinations, compositions or formulations, which elicit responses from cellular receptors, and more specifically to those compositions/formulations that comprise two or more receptor-activating, receptor-modulating or receptor-inhibiting molecules in specific ratio combinations to reduce or prevent one or more undesirable responses while maintaining or enhancing the primary or desired therapeutic response(s).

BACKGROUND OF THE INVENTION

Recognition of the potential for drug combinations has a long history in medicine. In the fields of pharmacology and toxicology, the concepts of synergy, chemical addition and antagonism have been explored, but without a concomitant development of successful pharmacological models that predict or explain these effects. Many doctors rely on combination therapies that have been proven successful as treatments for several diseases, but these combinations have not been rigorously optimized by any explicit scientific method. The heuristic testing of drug combinations is an accepted strategy for drug development and improvement without a concomitant understanding of the underlying scientific principles necessary for the discovery of optimal drug combinations. This has led to the heuristic and rather indiscriminate testing of combinations of drugs in patients as an explicit strategy for drug development and improvement.

Most of these new drug combinations are created from chemical agents already known to be effective for treating specific diseases or chronic conditions. Generally, combinations are created that seem intuitively beneficial because they have similar clinical endpoints; however, such combinations represent only a small fraction of the combinations possible and are unlikely to result in optimal therapeutics without knowing the pharmacological relationships between the drug concentration ratios and their corresponding therapeutic effects. In combination, two or more drugs may produce responses that are not at all similar to the activity of the individual components alone (similar to the way that colors can be combined to form another, distinct color such as by combining yellow and blue to make green). The biological effects of these combinations are not intuitively obvious even to those skilled in the arts of pharmacology, pharmacy, biotechnology or the pharmaceutical sciences. Since the variations in drug ratios within these combinations are relevant to finding the best therapeutic combinations, an efficient scientific method is needed to find these optimal therapeutic drug combinations.

In addition, one or more of the following mistakes are often made when creating or using various combination products:

1) Not making a specific ratio combination to test as a single combination product. This includes not pre-mixing and combining the individual components before testing.
2) Not testing the specific ratio combinations over the full range of the dose-response curve and comparing this to the dose-responses of the individual components alone.

For example, by not making a single specific ratio combination, the effects of adding another molecule or drug on the dose-response curve may produce an effect on the receptor response that is not quantifiable if the ratio of the combination varies or is unknown over the course of the experiment. A second example concerns not pre-mixing the molecules with sufficient care, which may subject the receptors to initially be in contact with only one component or in contact with varying combination ratios of the combination product, which may cause spurious observations. As a final example, the specific ratio combination should be treated as if it is a new drug entity that should be tested over a full dose-response range and compared with the dose-response curves over the same range for its individual components. Previously, those who have studied drug combinations have not studied them for their utility over the full dose-response range. Not considering the full dose-response range may hide dosage effects that need to be accounted for in comparison to the single drug alone.

Each of the three mistakes listed above produces experimental observations that do not fully or truly characterize these specific ratio combination products. The advantages and disadvantages of these specific combinations may be missed by incomplete dose-response information such as testing at a single dose that may not reflect the clinical use of the drug over time. By not addressing these three mistakes, most previous experiments claiming to find or test new properties of specific combinations have not done so in a complete or rigorous scientific manner.

Several scientists attribute the untoward effects of combinations on the combined effect of both drugs on the complex signaling networks that coordinate activity within and between cells. It is thought that using drugs in combination interrupts or modulates these intracellular networks at multiple points and influences cellular signaling networks in ways that the individual components cannot.

Although recent efforts have examined the benefits of combinatorial drugs for treating various diseases, there remain problems in modeling, understanding and controlling primary and secondary effects from such combinations. Pharmacology has yet to discover optimal methods that sufficiently characterize these changes that are produced in receptor systems. Simulations of the biological receptor responses created by fitting somewhat arbitrary and awkward computer algorithms or models to interdependent biological networks produce results that demonstrate synergistic effects but have limited predictive or conceptual value. However, system biology models are useful for systematically recording, displaying or mining such observations for possible therapeutic benefits or potential drug side effects.

Although these models attribute the untoward effects of drug combinations on their cumulative effects on intracellular signaling and metabolic networks, there is also evidence that these complex and untoward effects are generated at the very earliest interactions of drugs or molecular ligands with their complementary cellular receptors. Independent experimental observations have supported the suggestion that receptors contain free sulfhydryl groups that can be modulated by other molecules such as ascorbate, which may influence the sulfhydryl oxidation/reduction equilibrium thereby creating more active receptors and making the experimental preparation more sensitive to stimulating drugs such as norepinephrine.

Often, it is these early events in molecular recognition that guide the subsequent downstream and intracellular responses. The fact that these early receptor-activation events remain poorly understood and uncharacterized in most of the models used in systems biology or bio-informatics reduces the inherent validity of these models. By focusing on the systems biology approach alone, secondary activation events may be artificially created for intracellular signaling pathways that may be inaccurate and unnecessary.

The earliest events of receptor activation require the recognition of an extracellular signal that usually involves an endogenous agonist ligand activating its target receptor. As general models for receptor activation, the G protein-coupled receptors (GPCRs) have been studied extensively to understand the complex molecular changes that accompany receptor activation and signal transduction. Recent experimental discoveries have significantly changed our understanding of how these receptors work. It has been demonstrated that transgenic mice with an increased number of B2AR receptors exhibit spontaneous activity similar to normally expressed receptors in the presence of an agonist ligand.

This observation separated receptor activation from the action of agonist ligands alone and prompted a revision of receptor models to include an intrinsically active receptor state. One consequence of this revision was that the resting populations of receptors must interconvert by themselves from resting to active states. However, the biophysical basis for these active and inactive receptor states has not been adequately defined or understood.

Models that describe receptor activation use various mathematical techniques to depict the mathematical relationships between key receptor and drug-receptor species. Those models that use differential equations to capture the dynamic changes within these systems, miss the overall net changes produced by selective ligand binding to the populations of receptor states or alternative factors that can change these states such as a change in receptor number and constitutive activity. Many of these expressions can be made to fit the available data, but are difficult to extrapolate to meaningful biophysical data that predict biological responses.

In general, two-state mathematical models have been recognized to be among the most successful for describing receptor activation. Most of these models calculate either the proportional or fractional receptor occupancy as the overall receptor response. Although it is seductive to assume that the proportional amount of an active receptor state should correlate with the biological response, the experimental evidence for receptor overexpression and spare receptors suggests that the net change in the active receptor state is a much better measure for response than is the fractional or proportional change. This is also demonstrated by the experimental observations that agonist/antagonist combinations can reduce or prevent the desensitization of beta-receptors, which is not predicted by other models.

This is also demonstrated by receptors that are activated by overexpression since this requires a change between R and R* that is difficult to understand in terms of a proportional rather than a net change. One possible perspective is that there exists an initial equilibrium between the inactive and active receptor states that is perturbed by ligand binding to produce a shift in the net amounts of these states. An agonist ligand favoring the active receptor state perturbs the initial chemical equilibrium toward the higher affinity receptor state, thereby inducing receptor activation in a manner similar to Le Chatelier's principle.

From this perspective, it is important to determine within the constructs of any biophysical model what molecular states interconvert either by ligand stimulation, receptor overexpression, mutations or other modulating molecules or drugs. The model presented herein calculates this net change as a distinct parameter with biophysical parameters that have direct mathematical relationships to recognizable molecular receptor states. This model is the only one that takes this approach toward receptor activation. Those models that do not parameterize for a net change and use inappropriate or unrealistic biophysical parameters have difficulties in quantifying pharmacological responses in a meaningful way.

In parallel to the systems biology approach, recent developments in pharmacology have provided new insights into a variety of modulating signaling molecules or drugs that produce varied interactions with their targeted receptors, which, in turn, create a wide range of intracellular responses. Many if not most of these different signaling pathways are initiated by the earliest differences in ligand-induced intermediate molecular conformational states produced when ligand molecules bind to their target receptors, as shown for the beta-2-adrenergic receptor and for the 5-HT2A receptor. Other possible mechanisms may include the promiscuity of the receptors' interactions with a diversity of G proteins and other signaling partner proteins that couple with these receptors as well as receptor structural changes that include phosphorylation, palmitoylation, glycosylation, thiol modification, ubiquitination and/or oligomer formation.

These intracellular responses may include, but may not be limited to, the alteration of kinase/phosphatase activities, arrestin binding or unbinding, ubiquitination, phospholipase activities, methylation/demethylation, the modification of post-translational proteins and various peptidase activities as well as many other intracellular signaling cascades or enzyme reactions too numerous to mention here. The alteration of these intracellular response pathways by externally acting molecules and drugs often activate multiple intracellular effects such as an enzyme together with a kinase that subsequently phosphorylates other proteins within the cell. These signaling molecules include those labeled as "protean agonists" and those that demonstrate "functional selectivity" in their varied sets of receptor responses. Such studies have recently led to a redefinition of the concept of efficacy such that ligands can produce multiple stimuli (have multiple intrinsic efficacies) upon interaction with a receptor and can differentially regulate each of multiple signaling pathways coupled to a receptor. This ligand behavior has been termed "protean agonism", "agonist-directed trafficking of receptor stimulus", "functional selectivity", "conformational cafeteria", "pleiotropy", "stimulus trafficking", and "biased agonism". The underlying mechanism for this is proposed to be based upon the capacity of ligands to promote unique, ligand-selective receptor conformations that have differential efficacy to regulate signal transduction pathways.

Many important bio-pharmaceutical molecules or drugs differentially activate signaling pathways mediated by the G protein coupled receptors (GPCRs) and several other cellular receptors, such as the ion channel linked or ionotropic receptors, the tyrosine kinase and toll-like receptors. Experimental data illustrating these phenomena are known from the serotonin, angiotensin, vasopressin, adrenergic, opioid and dopamine receptor systems among others. Functionally selective ligands may often produce secondary responses due to cross receptor and intracellular effector signaling pathway stimulation, or due to the allosteric effects that some pharmaceutical molecules demonstrate by activating, modulating or otherwise altering other cellular targets or sites. The principles of allosterism in reference to drug action are important in the ionotropic and G-protein coupled receptor systems, which encompass the GABAA, GABAB, 5HT3, nicotinic, ionotropic and metabotropic receptors for glutamate, muscarinic and alpha 2 adrenergic receptors. As these effects become better characterized with meaningful biophysical parameters, a suitable method to account for these effects is important in order to design an optimal technique to minimize, reduce and/or block those effects that may be detrimental to the overall therapeutic response of many important bio-pharmaceutical molecules or drugs.

SUMMARY OF THE INVENTION

The method of the present invention demonstrates the utility of combining biological or pharmaceutical molecules or drugs into specific ratio combinations that improve the overall therapeutic safety and efficacy of the individual drugs alone. This method includes the combining of two or more drugs or modulating molecules with another drug or biological or pharmaceutical agent into a specific ratio combination. These specific ratio combinations are designed to function over the full dose-response range to enhance the safety and efficacy of biological or pharmaceutical drugs and other receptor stimulating or modulating molecules. These specific ratio combinations are also designed to control or modulate different intracellular signaling pathways to optimize the therapeutic response.

Controlling or modulating such differentially activated signaling pathways would have a clear impact on drug discovery, as this mechanism raises the possibility of selecting or designing novel molecular combinations that differentially activate only a subset of functions of a single receptor, thereby optimizing the therapeutic actions of various drugs. Several incomplete models describing these effects have been previously introduced with complex parameters that do not correspond to appropriate biophysical parameters. These models have difficulties explaining and/or predicting the biological responses from signaling networks exposed to molecular combinations such as agonists in combinations with antagonists, inverse agonists, negative antagonists or other modulating molecules or drugs. Currently there is no overall scientific methodology to control or modulate these varied interactions using specific molecular combinations. The method of the present invention solves this problem by using measurable biophysical parameters to describe and subsequently control these various responses using specific ratio combinations that minimize the signals that produce unwanted side effects while maximizing the desired signals produced by biological receptor systems.

The stimulation of secondary biochemical pathways within the cell often creates unwanted side effects of many biological or pharmaceutical medicines and drugs. One possible strategy to prevent these secondary pathways requires the intracellular applications of various types of molecules. However, the overall safety of this approach may be questioned due to the inability to quickly and safely reverse such intracellular applications or therapies. As a safer alternative, the method of the present invention proposes to modulate these intracellular pathways with reversible applications of molecules that mostly target the external cellular receptors rather than those molecules and signaling pathways within the cells. This approach may also prove to be more benign than artificially altering intracellular pathways without concomitant receptor stimulation.

The method of the present invention proposes several ways to rationally combine known drugs for either improving their efficacy or suppressing individual side effects. Toward this goal, the method teaches how to combine biological or pharmaceutical molecules or drugs in order to create specific ratio combinations that improve the overall safety and therapeutic efficacy of the individual molecules or drugs alone. These techniques may also create novel modes of receptor activation that may prove useful for future therapeutic treatments. This model represents significant improvements over previous models in its ability to handle inverse agonists, negative antagonists as well as other modulating molecules in combinations. It can also model the actions of these molecules alone and in combination to produce primary and secondary intracellular and physiological effects. The model also demonstrates how molecules that produce either up-regulation or down-regulation of the functional pool of receptor molecules can modulate the overall receptor response. To my knowledge, there is no other method or model that can currently model all of these situations.

Examples are provided herein where the method of the present invention is used to predict unexpected results that have been experimentally demonstrated. Further examples will show how the method of the present invention greatly reduces the relative stimulation of secondary intracellular pathways that lead to unwanted side effects. Additional examples will show that the method of the present invention creates drugs or biological or pharmaceutical medicines with enhanced efficacies and safer therapeutic profiles. This can encompass the modulation of many different types of cellular receptors such as are listed in respected pharmaceutical depositories.

The model embodied in the method of the present invention represents several significant advances over previous models and describes many aspects of the drug-receptor response that have previously eluded description in a single biophysical model. These advances include: (1) a relatively simple biophysical model that shows the full range of the drug-receptor response with suitable parameters that model multiple side effects together and apart from the effects of other modulating molecules or drugs; (2) a scientific method to predict drug-receptor responses that models the experimentally determined data with meaningful biophysical parameters; (3) a specific method to determine the receptor specific effects of combining drugs of varying efficacies and affinities on the overall drug-receptor response; (4) a method that demonstrates how to selectively modulate the receptor response to encompass responses or a specific response from the full range of all possible receptor responses; (5) a scientific method to determine the specific ratio drug combinations that modulate a targeted receptor response to accomplish the enhancement of standard pharmacological or medical treatment with hormones, peptides or drugs by; (a) the prevention or reduction of unwanted side effects such as arrhythmias, desensitization, tachyphylaxis, tolerance, down-regulation, autoinhibition, fade, subsensitivity, wearing-off, resistance, receptor internalization, phosphorylation/dephosphorylation and/or unwanted modulation; (b) the enhancement of the response to endogenously produced hormones and/or metabolites by increasing the desired therapeutic response; (c) the enhancement of cross receptor modulation by either increasing or decreasing the desired therapeutic response while simultaneously either increasing or decreasing the undesired secondary responses; and (d) the accurate titration of medically desired endpoints using drug combinations that modulate targeted receptor responses; and 6) a method to design partial agonists by combining full agonists with antagonists or with other partial agonists. The method of the present invention may be specifically applied to molecules and drugs generally classified as agonists, antagonists, partial agonists, inverse agonists, negative antagonists, partial negative antagonists, partial inverse agonists, partial negative antagonists, partial inverse agonists or neutral antagonists as well as other molecules that can modulate, stimulate or block receptor responses.

In some cases, it may be therapeutically advantageous to choose a sub-optimal dosage for specific drug combinations in order to control or ameliorate the unwanted side effects of particular biological or pharmaceutical medicines or drugs. Under certain circumstances, it may be therapeutically advantageous to design a drug that produces a somewhat less than maximal response. This will be described in more detail below. The method of the present invention modulates all of the drug-receptor responses in order to take into consideration the undesirable side effects or secondary interactions of biological or pharmaceutical drugs and medicines together with their desirable effects. An important aim 1s to selectively modulate those intracellular pathways that ultimately determine the physiological responses of targeted biological and physiological systems. Choosing which pathways to enhance and which pathways to reduce requires expert knowledge of these complex systems and how they ultimately affect the treatment of patients. However, the method of the present invention gives the power to modulate and otherwise control these systems to those skilled in the art.

The recognition of ligand-selective receptor conformations opens the possibility of designing drugs that modify only portions of a given receptor's behavior and thereby produce an improved therapeutic profile. In the drug discovery process, often a partial agonist profile is the preferred chemical target. For example, in asthma, the bronchodilator properties of beta-adrenoceptor agonists need to be separated from the cardiac stimulatory and digital tremor properties of these agonists. These agonist-selective receptor conformations offer yet another dimension to design better therapeutic agonists. In this regard, the method of the present invention offers new ways to design partial agonists by combining full agonists with antagonists or with other partial agonists. This greatly simplifies the drug discovery process in that the preferential receptor conformations can be designed by combining existing drugs rather than by time consuming, laborious and uncertain molecular design de novo.

The method of the present invention demonstrates how to control receptor responses by combining the interactions of various biological or pharmaceutical drugs and medicines that together can achieve improved therapeutic responses useful in medicine to treat a wide variety of diseases. In several ways, the method of the present invention is superior to those methods that seek to modulate internal cellular pathways using intracellular techniques that are not as readily reversible as the application of externally acting molecules or drugs. The method of the present invention may be reversed by the selective use of inhibitors or washed out of the system by various physiological or pharmacological interventions as are commonly used for the treatment of a drug overdose. Therefore, by modulating the receptors of cells to indirectly control the intracellular biological systems of specific cells and physiological systems, the method of the present invention presents an inherently safer way to accomplish these important therapeutic goals.

The invention and its particular features and advantages will become more apparent from the following detailed description considered with reference to the accompanying drawings.

DETAILED DESCRIPTION OF AN EMBODIMENT OF THE INVENTION

Figure 1:
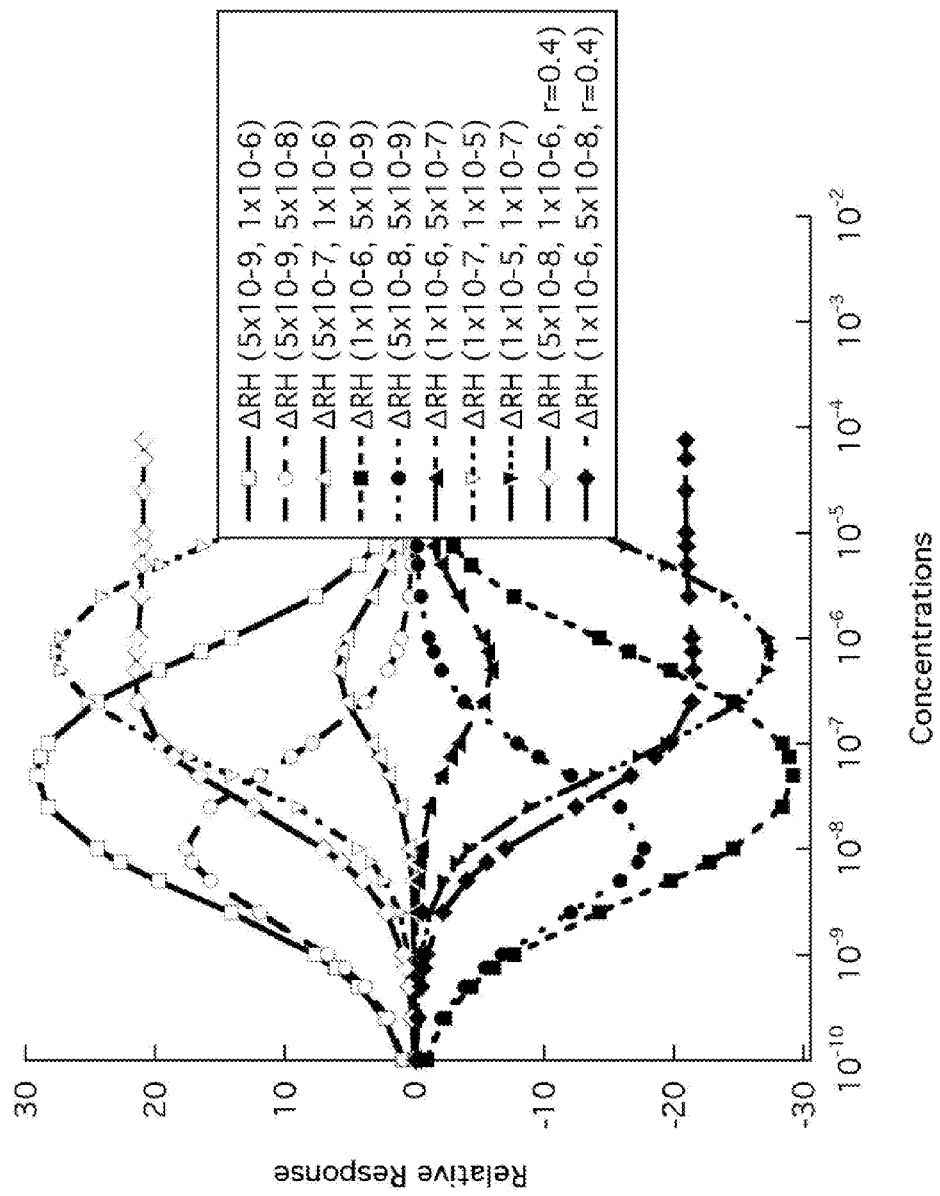
FIG. 1 depicts a sample of the ranges of complex receptor responses that are described by the model embodied in the method of the present invention.

Receptor activation requires, in its earliest step, the recognition of an extracellular signal that usually involves an agonist, or activating ligand, binding with its target receptor. Binding alone is not sufficient to activate receptors since competitive antagonists, which can inhibit agonist binding, are generally very good at binding, but fail to produce an activation response. This suggests that the functional selectivity of molecular ligands begins at the earliest stage of receptor activation.

As general models for receptor activation, the G protein-coupled receptors (GPCRs) are extensively studied in order to understand the complex molecular changes that accompany receptor activation and signal transduction. Recent experimental discoveries have significantly changed our understanding of how these receptors work. Studies have demonstrated that transgenic mice with an increased number of B2AR receptors exhibited spontaneous activity similar to normally expressed receptors in the presence of an agonist ligand. This observation separated receptor activation from the action of agonist ligands alone and prompted a revision of receptor models to include an intrinsically active receptor state. One consequence of this revision was that the resting populations of receptors must interconvert by themselves from resting to active states. However, the biophysical basis for these active and inactive receptor states has not been adequately defined or modeled.

One point of view is that there is an initial steady state or equilibrium between the inactive and active receptor states that is perturbed by ligand binding to produce a net shift or perturbation in the amounts of these states. An agonist ligand favoring the active receptor state perturbs the initial receptor equilibrium toward the higher affinity receptor state, thereby inducing receptor activation in a manner similar to Le Chatelier's principle.

It has been recognized that in general, the two-state mathematical models have been among the most successful for describing receptor activation. Most of these models calculate either the proportional or fractional receptor occupancy as the overall receptor response. This has led to some difficulties in understanding the nature of the net shift in the initial populations of the receptor states that most likely occurs for receptor activation.

Models Embodied in the Method of the Present Invention

Although it is seductive to assume that the proportional amount of an active receptor state should correlate with the biological response, the experimental evidence suggests that it is the net change in the active receptor state that is a much better measure for response than is the fractional or proportional change. This is clearly demonstrated by several experimental observations of agonist/antagonist combinations on the desensitization of beta-receptors not predicted by other models and by receptors that are activated by overexpression since this requires a change between R and R* that is difficult to model or understand in terms of a proportional rather than a net change.

From this perspective, it is important to determine within the constructs of any biophysical model what molecular states interconvert either by ligand stimulation, receptor overexpression, mutations, or other modulating molecules or drugs. The model presented herein and embodied in the method of the present invention calculates the net change as a discrete parameter. This model contains meaningful biophysical parameters that have direct mathematical relationships to recognizable molecular receptor states. Those models that do not parameterize for a net change with inappropriate or unrealistic biophysical parameters have difficulties in quantifying pharmacological responses in meaningful ways.

Figure 9:
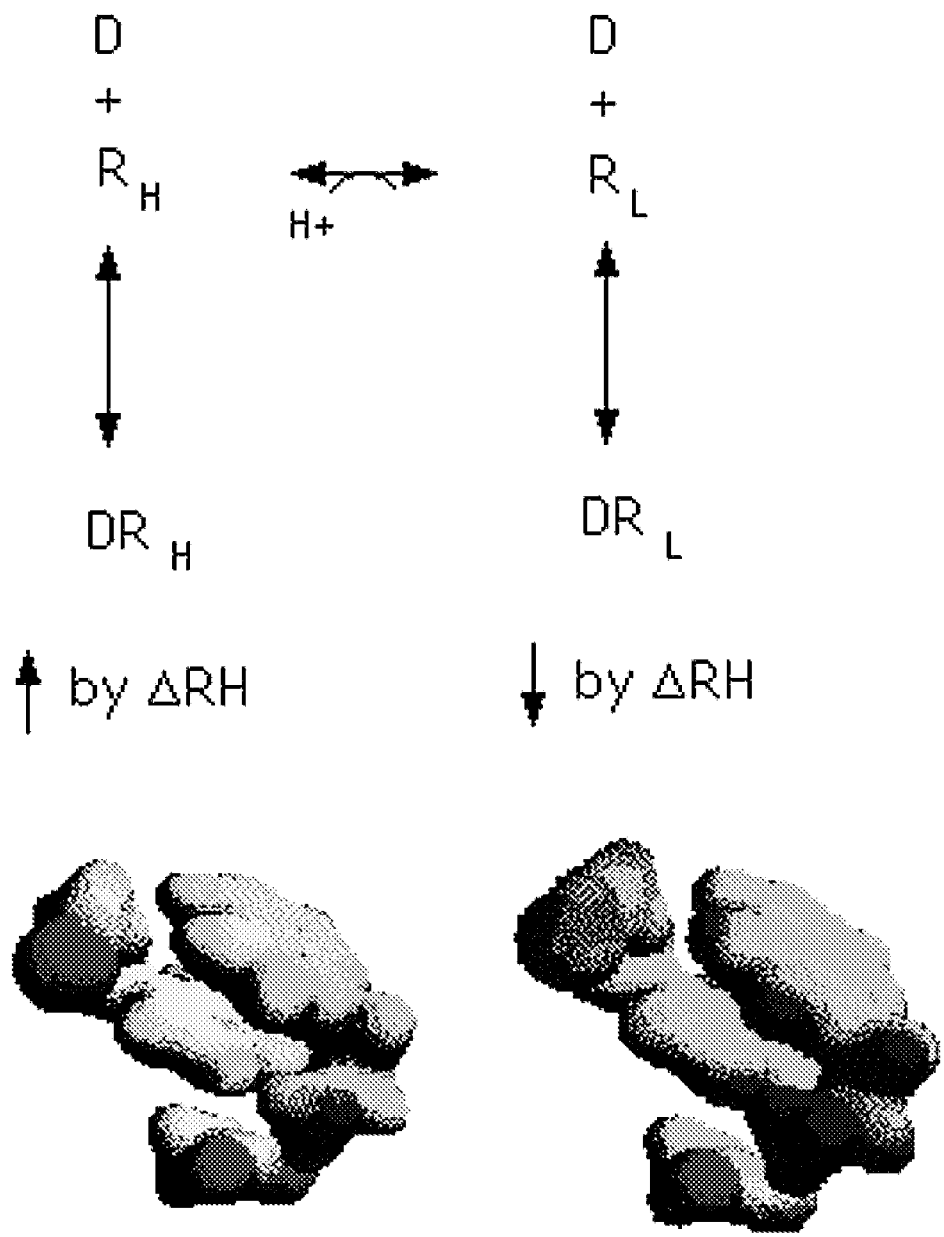
FIG. 9 shows the relationship between the molecular and mathematical models embodied in the method of the present invention.

FIG. 9 shows the relationship between the molecular and mathematical models, and more specifically shows how the binding of a drug molecule D could perturb the amounts of $R_H$ and $R_L$ to produce a net enrichment of the active state. This mathematical model calculates a discrete change, $\Delta RH$, that measures the perturbation of the $R_H$ and $R_L$ initial steady state or equilibrium ratio. On the molecular level, the two receptors states $RS^-$ and $RSH$ with the bound drug ligand, D, shown in the figure on the left and right respectively, correspond to the mathematical states, $DR_H$ and $DR_L$.

The shading of the molecular models represents the electrostatic potential energies for these two bound states. In general, the lighter shading of the molecular model to the left represent a negative electrostatic potential, while the darker shading of the molecular model to the right represents a positive electrostatic potential. The electrostatic interaction energy differences between these molecular states correspond to the experimentally measured ligand efficacies in several different receptor systems. In the mathematical model, drug efficacy is generated by the difference in the affinities of the drug for the two receptor states ($K_{DL}-K_{DH}$). This is compatible with the findings from the molecular model if one considers that the electrostatic interactions are the primary contributors to a drug's affinities for each receptor state.

In addition to the drug-receptor binding, $DR_H$ and $DR_L$, there is also the equilibrium, or steady state, between the two, high and low affinity, receptor states, $R_H$ and $R_L$. This equilibrium, or steady state, can be perturbed by modulating molecules that directly or indirectly determine the amounts of $R_H$ and $R_L$. For example, if the relative ratios of $R_H$ and $R_L$ are pH-dependent as originally hypothesized, then molecules that alter the affinities of different receptor residues may also indirectly or allosterically modulate the affinities of drugs and/or molecules that bind to the orthosteric or primary binding site. Alternatively, molecules that change the oxidation/reduction ratios of receptors may increase or decrease the number of functional receptors. These examples argue for a modulation factor, $m_i$, that adjusts the amounts of $R_H$ and $R_L$ without having to consider the ensembles of all possible microstates, which would add undue and unnecessary complexity to any useful model.

In the absence of drug, D, the initial thermodynamic functions partition the relative amounts of $R_H$ and $R_L$ such that an equilibrium constant $K_R$, can be described as:

$$K_R = \frac{[R_H]}{[R_L]}$$

Technically this should be referred to as a reaction quotient, because most biological systems do not reach a true equilibrium. However, since the term equilibrium is most commonly used it will be used in the subsequent description.

The chemical equilibrium expression for $K_R$ depends upon how we label the $R_H$ and $R_L$ chemical species. The single $[R_H]$ or $[R_L]$ concentration incorporates a diverse and rather large number of possible microstates. Realistically, a molecule in solution could have various counterions, enantiomers, conformations, hydrogen bonded waters and trace molecules present that would all measure the "$R_H$" or "$R_L$" chemical species. These various forms would likely be more numerous for larger and more complex molecules such as proteins. Since we do not know each of the separate micro-equilibria for each microstate, we implicitly include these together into the equilibrium expression. The point being that our measurement of the $R_H$ chemical species is based upon what we measure not what we know. Our knowledge of the microstates and their equilibria is combined into the macroscopic measurement $[R_H]$. Therefore, we should realize that our understanding of the equilibrium concentrations are imperfect and in fact represent series of coupled equilibria that we combine into one expression for a concentration. Therefore, the expressions for $[R_H]$ and $[R_L]$ represent a collection of many microstates that for convenience are lumped together.

The idea that there is an ensemble of various protein conformations that a given receptor presents to ligands has been termed the "conformational cafeteria." Molecules influence the overall receptor response through their selective affinities for the various receptor conformations or potential conformations.

In this way, a binding ligand or drug shifts the equilibrium towards those conformations that have the greatest affinities for a particular ligand. This produces net changes in the initial receptor states that determine further binding of the receptor with subsequent molecules and proteins. This most likely involves a plethora of possible molecular states that lead to protean responses from interacting ligands that can not be entirely encompassed by any useful mathematical or molecular models. However, by choosing appropriate biophysical reference states, a reasonable biophysical model can be constructed that demonstrates both the quality and quantity of these net shifts in receptor states.

Various counter-ions, oxidation/reduction and pH-changes of secondary residues represent many different micro-equilibria that couple with these "$R_H$ and $R_L$" states. These changes may require a deeper understanding of how the underlying equilibria interact and combine with each microstate within the overall equilibrium. This raises a much more complicated question than we can discuss here. However, we can study such chemical perturbations in more accessible systems that are more tightly controlled. Ironically, the membrane-embedded, cellular receptor may be such an ideal system to model these chemical perturbations directly.

I have importantly discovered that the effects of many modulating interactions can be modeled empirically by introducing a new parameter, $m_i$, for each region shown where modulating molecules influence the overall response of the receptor system without introducing complex binding equations for each molecular state or microstate. Using $K_R$ as a reference point, modulators for this system can affect four points in the system as diagramed below.

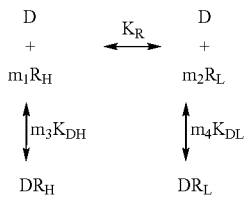

In the presence of drug, D, and modulators, $m_i$, the ratio can be perturbed in two equivalent ways such that the final ratios remain equal. One way that this can be expressed as mathematically equivalent ratios is:

$$\frac{[m_1 R_H] + [DR_H]}{[m_2 R_L] + [DR_L]} = \frac{[m_1 R_H] + \Delta RH}{[m_2 R_L] - \Delta RH}$$

where the $m_i$ represent the effects of one or more modulators and $\Delta RH$ represents the net change that occurs between the initial $[R_H]/[R_L]$ ratio produced by the formation of the additional $DR_H$ and $DR_L$ states. Solving for $\Delta RH$ yields:

$$\Delta RH = \frac{[m_2 R_L][DR_H] - [m_1 R_H][DR_L]}{[m_1 R_H] + [DR_H] + [m_2 R_L] + [DR_L]} \quad (1)$$

This is a more complex version of a fundamental equation for measuring the equilibrium change between competing chemical species similar to the poised equilibrium derived for a two-pan beam balance, which under Langmuir binding conditions obeys the well-known Weber-Fechner Law.

The initial binding of D is determined by the initial concentrations of $R_H$ and $R_L$ and the affinity constants $K_{DH}$ and $K_{DL}$ that D has for $R_H$ and $R_L$ respectively. Under the constraints imposed by these initial conditions the amounts of $DR_H$ and $DR_L$ can be described by the two Langmuir binding expressions:

$$DR_H = \frac{m_1 R_H [D]}{[D] + m_3 K_{DH}} \text{ and } DR_L = \frac{m_2 R_L [D]}{[D] + m_4 K_{DL}}$$

These functions determine the amount of the initial binding of D to $R_H$ and $R_L$. If there are no modulators, m, and $K_{DH} = K_{DL}$ then the binding of D will not perturb the initial ratio of $[R_H]/[R_L]$. If $K_{DH} \neq K_{DL}$, then the initial binding of D to $R_H$ and $R_L$ will be relatively unequal, which will perturb the initial ratio of $[R_H]/[R_L]$. The stress on the original equilibrium from the binding of S produces a perturbation (given $K_{DH} \neq K_{DL}$). The origin of this perturbation is the relatively unequal binding of D to $R_H$ and $R_L$. It may be worth noting that if modulators are present, then even if $K_{DH} = K_{DL}$ the influence of the modulators may perturb the original equilibrium if $m_3 K_{DH} \neq m_4 K_{DL}$.

Modulating molecules, m, may produce many effects at various regions of the overall drug-receptor two-state binding expression. These effects may often occur at the earliest binding of the drug with its target receptor. A list of the potential ways that modulating molecules can alter the drug-receptor interaction will help to give the full scope of this model.

A list of some of the possible modulating expressions for m include:

$$m = (1 + ([I])/K_i)$$

$$m = (1 + (r[D])/K_i)$$

$$m = r[D]$$

$$m = r$$

A modulating molecule may function as an inhibitor or neutral antagonist. At a fixed dose, it can be represented mathematically as $m = (1 + ([I]/K_i)$ multiplied times each of the dissociation constants $K_{DH}$ and $K_{DL}$. If it is given as a specific ratio to the drug, "D", then it is represented as $m = (1 + (r[D]/K_i)$ multiplied times the dissociation constants $K_{DH}$ and $K_{DL}$. A modulating molecule may also represent some amount, r, that alters the amounts or relative amounts of another molecule such as r[D] which could represent some fraction of [D] that produces an effect at another molecule or point in the system.

Modulating molecules may also produce effects on the receptor states themselves by altering the amounts and types of receptor configurations due to their allosteric or orthosteric binding that may regulate such things as the oxidation/reduction state of the receptors or the pH-dependence or the surface ionic charge or the coupling with other membrane lipids, proteins or counterions. These modulating effects will affect the amounts of $R_H$ and $R_L$, which in turn will affect $\Delta RH$. Therefore, to account for these effects the modulating factor, m, is introduced into the full expression for $\Delta RH$.

In order to calculate the net perturbation, we can substitute the two Langmuir binding expressions for $DR_H$ and $DR_L$ into Equation (1) to get, $$\Delta RH = \frac{[m_2 R_L]\frac{m_1 R_H [D]}{[D] + m_3 K_{DH}} - [m_1 R_H]\frac{m_2 R_L [D]}{[D] + m_4 K_{DL}}}{[m_1 R_H]\frac{m_1 R_H [D]}{[D] + m_3 K_{DH}} + [m_2 R_L]\frac{m_2 R_L [D]}{[D] + m_4 K_{DL}}}$$

and further simplifying gives, $$\Delta RH = \frac{m_1 R_H m_2 R_L (D)(m_4 K_{DL} - m_3 K_{DH})}{m_1 R_H (2D + m_3 K_{DH})(D + m_4 K_{DL}) + m_2 R_L (D + m_3 K_{DH})(2D + m_4 K_{DL})} \quad (2)$$

where $R_H$ and $R_L$ represent the two states of the receptor and D represents the concentration of the binding drug or ligand. This expression compares the two Langmuir binding functions with the modulators, $m_1$, $m_2$, $m_3$, $m_4$, $DR_H$ and $DR_L$, for their relative effects on the ratio of $[R_H]$ to $[R_L]$. This allows us to measure the net change when the binding of any modulator or D to $R_H$ and $R_L$ perturbs the original chemical equilibrium.

The use of modulators has a long history in pharmacology. Although modulator parameters were often added to account for their effects on the binding affinities of ligands to the hypothesized receptor states, those models did not consider the net perturbation in the receptor system. However, the model embodied in the method of the present invention quantifies the net perturbation and extends the modulators' usefulness to modify the $R_H$ and $R_L$ states in addition to the binding affinities. This extension is based upon many experimental observations that show that various modifiers can change the net amounts of $R_H$ and $R_L$. For example, modulators that alkylate or modify the oxidation/reduction ratios or the pH-dependence of the receptors may increase or decrease the number of functional receptors and alter the relative ratios of $R_H$ and $R_L$.

By measuring the net influence of two Langmuir binding functions competing for each receptor state in a poised chemical balance, I have developed a mathematical tool to measure the net change, which quantifies the conformational selection as previously discussed in the prior art. In the specialized situation where an increase in receptor numbers produces constitutive activity, substituting $2R_H$ and $2R_L$ into Equation (2) for a representative doubling of the total amount of receptors (with an equal apportionment between the $R_H$ and $R_L$ states) would give a net $2\Delta RH$, suggesting a doubling in the net change, which is in general agreement with experimental observations.

Additionally, the total ligand binding can be seen as the sum of the Langmuir binding to each state, which provides a mechanism to explain the phenomena of spare receptors. This approach also explains why there is a close correlation between the thermodynamic coupling free energy for a two-state acid-base model and the experimentally determined efficacies for ligands binding to the 5-HT$_{2A}$ receptor.

Interestingly, the left hand side of the ratio $$\frac{[m_1 R_H] + [DR_H]}{[m_2 R_L] + [DR_L]} = \frac{[m_1 R_H] + \Delta}{[m_2 R_L] - \Delta}$$

can be thought of as a ratio of the sums of the probabilities of the high affinity or active states over the probabilities of the lower affinity or inactive states, which is somewhat similar to a thermodynamic partition function with the relative ratio of the probabilities summed over all states. In the ratio expression, the denominators would cancel to give the left hand side of this ratio.

Although previous theories have discussed the probabilistic model of receptor function, they have two major problems in their fundamental ideas concerning the pharmacological concepts relating affinity to efficacy. The first problem is that they have not found or selected a suitable reference state of the receptor with which to compare the changes to the populations of receptor microstates, and the second is that they refer to the effect of a ligand on changing the ratio between the active and inactive receptor states rather than calculating the net change. This confuses the demonstration of a ligand's efficacy with its potential for altering the relative populations of receptor states.

As an example, suppose that there exists a pool of quiescent receptors (such as thiol alkylated) that become active in the presence of a ligand that chemically reduces these receptors to form more potentially active receptors. This would not necessarily change the relative ratio of the active and inactive receptor states, but it would increase the net amount of receptors and thereby increase the net amount of the active receptor state ($\Delta RH$); thereby showing efficacy under the model embodied in the method of the present invention, but not under other previously known models as described above. One could reverse this argument for a ligand that alkylates the receptor. These are additional arguments for the net change being a better measure for receptor activation and thereby ligand efficacy than the proportion or ratio between the active and inactive receptor states.

However, while the proportion or ratio between the active and inactive receptor states does provide a good representation of the underlying thermodynamic and probabilistic nature of these states, unless the biophysical nature of the active receptor state is known, it is difficult to understand how various ligands can interact with receptors in a large number of ways to produce some conformations that induce an active state. The model embodied in the method of the present invention overcomes these problems by demonstrating a feasible biophysical model that has the base form of the receptor as an active receptor state together with a mathematical derivation for the net change in this active state, and thus presents a comprehensive model with all of the elements necessary for a better understanding of the therapeutic receptor response.

The Method of the Present Invention

In order to understand and model the responses of modulatory molecules and drugs interacting with receptors in accordance with the method of the present invention, the first empirical step is to measure routine dose-response data with and without fixed dosages of the molecules or drugs to be tested. The second step is to enter this experimental data into the biophysical model in order to calculate the appropriate biophysical parameters from the model. Once these are obtained, then the model is used to recalculate the desired results to form a specifically calculated ratio combination of the molecules or drugs. The model allows us to predict the responses of these drugs and molecules when used in specific ratio combinations. Using this method to describe the modulation of receptors with one or more additional molecules, allows one skilled in the art to maximize the desired response while minimizing the unwanted responses to specific ratio combinations of the modulatory molecules with bio-pharmaceutical medicines or drugs.

This method reduces side effects to a targeted level. Alternatively, with the proper molecular combination, the method can be used to enhance drug efficacy. This method allows one skilled in the art of pharmacology to see the gain in efficacy produced by a specific ratio combination and to reduce concomitant side effects that may accompany such modifications. If there is a targeted receptor system useful in some therapeutic capacity that also produces a particular secondary response that is not desired, then reducing or eliminating this secondary response may produce a better therapeutic response. By selecting a targeted reduction in the secondary response less than some relative response value such as a twenty-five percent reduction, the specific ratio combination "r" necessary to achieve this without undue inhibition of the primary or desired response can be calculated using this method.

Although there are many models of receptor activation, none have developed a biophysical two-state theory that calculates the discrete change in receptor states as a quantifiable parameter that determines the ligand induced perturbation in the equilibrium receptor states coupled with the variable affinities of other modulatory molecules or drugs in specific ratios with the original first drug or ligand molecule, and consequently, no one has developed the instant and exacting method for determining actual drug compositions based upon a specific ratio of drugs with other modulating molecules or drugs.

The specific ratio, "r", is another parameter introduced into the model embodied in the method of the present invention to represent the specific ratio of the modulating molecule to the reference drug. This specific ratio alters the behaviors of many drugs in ways that have not been previously predicted over the dosage range of the drug. In addition, this model also allows for variable affinity constants that modulating molecules might have for each state of the receptor. These new biophysical parameters allow this model to describe and predict receptor responses that have not been previously fully characterized or modeled with such accuracy with appropriate biophysical parameters.

The model embodied in the method of the present invention also provides a way to design partial agonists by selecting specific ratio combinations comprising an agonist with an antagonist, inverse agonist or another partial agonist. This creates a new partial agonist composition that may have superior therapeutic effects compared to the agonist or a single molecule partial agonist alone. This also suggests that partial agonism occurs due to one or more conformations that either inhibit the fuller agonist conformations of a molecule that would otherwise function as a full agonist, or in contrast, provide active conformations to a molecule that would otherwise function as an antagonist. In general, the model handles these contingencies by using the appropriate modulator functions. However, the model does show partial agonism when the $K_{DH}$ and $K_{DL}$ constants are close to each other. This partial agonism will, however, also show desensitization all else being equal.

In the model embodied in the method of the present invention, the essential relationship between a drug's affinity and efficacy is due to the difference between the sum and the relative difference of the drug's Langmuir binding to each receptor state. This model also models the standard responses due to competitive antagonism and a reduction or increase in receptor number. This model represents a simple way to model multiple drug-receptor responses with multiple modulators. To my knowledge, this is the only model that can handle multiple modulators and multiple secondary interactions in order to determine optimal therapeutic responses from combinations.

EXAMPLE 1

FIG. 1 shows some of the ranges of complex receptor responses that are described by the model embodied in the method of the present invention. The responses are graphed as the relative response versus the concentration of drug, "D". In general, those responses that produce a positive stimulus for a specific biological function are shown as the unfilled symbols and those responses that produce a negative stimulus are shown as the filled symbols. These negative responses may correspond to "negative antagonists" or "inverse agonists".

Although one might think that the multiple responses are from multiple molecules, the increasing evidence for multiple responses from single molecule stimulation suggests that in the future, this Figure may represent the multiple responses for a single drug.

Because the response, $\Delta RH$, is comprised of the drug or ligand binding to the two receptor states, $R_H$ and $R_L$, there is the opportunity for other binding molecules to modulate the apparent affinities of the drug for these two states. The efficacy producing term in the main equation (2) is the ($K_{DL}$-$K_{DH}$) term in the numerator. The total binding is the sum of the separate Langmuir binding expressions for $D_{RL}$ and $D_{RH}$. A more in depth discussion of pharmacological theory would not be practical here, but this model is unique in that it measures the net change that occurs for any ligand with unequal affinities binding to the two receptor states. As shown by the complexity of FIG. 1, this rather simple system is able to account for the panoply of receptor responses. When taken together as the potential representations for a single molecule binding to its target receptor that, in turn, may activate several secondary pathways with varying signal strengths and forms as graphed in FIG. 1, a biophysical rationale for the protean natures observed for many drugs is suggested. Subtle conformational differences in the way fairly similar molecules interact with receptors may alter the subsequent strength and form of the receptors' binding to G proteins and other intracellular modulators that determine the intricate web of biochemical pathways that have had billions of years to adjust to subtle molecular signals.

In addition, there are additional modifications that may occur. Since the molecule, "D", represents a collection of various conformations in solution that interact with the various conformations of the receptor molecule, some of the conformations of the drug coupled with the receptor may not activate the receptor as well as others. There may exist portions from the conformational space of molecule "D" that act as inhibitory or modulatory molecules. This can be accounted for in this model by the parameter, "r", which represents the relationship between the ratio of the modulators, or antagonists, to the total concentration of the stimulating molecule ("[D]"). As an example of this, the FIG. 1 shows a positive and negative example for the response, $\Delta RH$, with r=0.4. Such modulation is important to consider for preventing or reducing unwanted secondary effects as demonstrated by the example given below.

EXAMPLE 2

Figure 2:
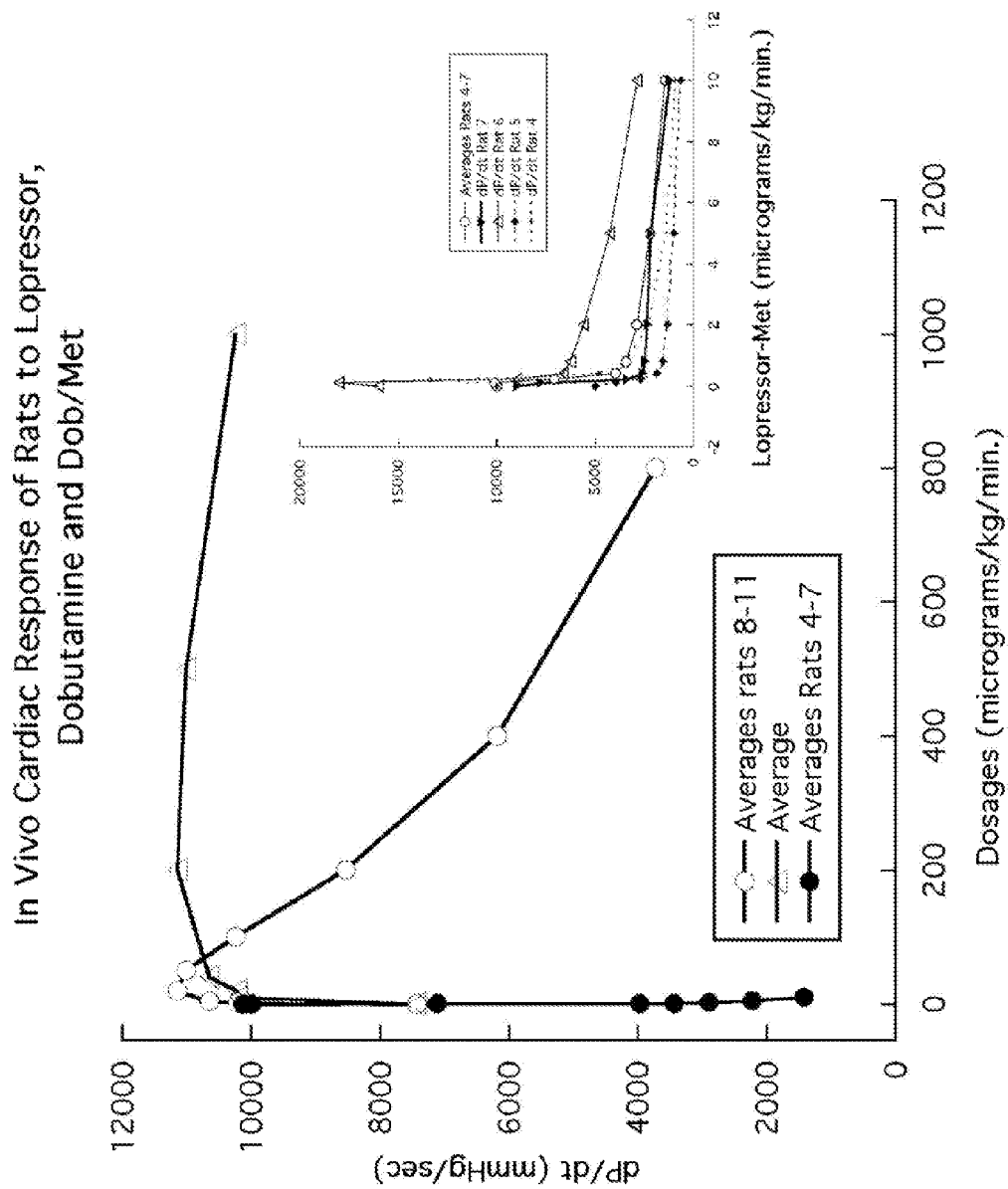
FIG. 2 presents empirical data of the in vivo response of rats to Lopressor® (the brand name for metoprolol used by Novartis Pharmaceuticals Corporation), dobutamine and the dobutamine/metoprolol specific combination ratio (Dob/Met)

In FIG. 2 titled "In Vivo Response of Rats to Lopressor, Dobutamine and Dob/Met", the response curve for Lopressor® (the brand name for metoprolol used by Novartis Pharmaceuticals Corporation) is displayed as the dark circles and also given with more detail as the inset graph for four individual rats. The Lopressor® acts much like an inverse agonist or negative antagonist in that it produces a steep decrease in the animals' dP/dt, which is a measure of the contractility of the heart. Although in this experimental context metoprolol may be inhibiting the sympathetic tone of these animals due to the production of their endogenous catacholamines, it functions much like an inverse agonist or negative antagonist. The data is plotted as the dP/dt response versus the dosages of the drugs or combination (dobutamine with metoprolol, Dob/Met). The average beginning baseline response was about 7400 mmHg/sec. From this baseline, the Lopressor® decreased dP/dt to below 2000. For the agonist, dobutamine, the average response for the rats labeled 8-11 are plotted with the unfilled circles. At doses below about 50 micrograms/kg/ min, the responses rise to a peak value of about 11000 mmHg/sec, but at further dosages these values decline to below 4000 mmHg/sec.

Examining the responses of metoprolol (Lopressor®) and dobutamine alone, one might think that in combination they would produce a more profound decline in the response to well below 2000 mmHg/sec. However, when they are mixed together in about a one to one molar ratio combination (as determined to be an appropriate ratio by employing the method of the present invention) and then administered as this specific ratio combination in the same dosages as for dobutamine alone, we see that they produce a maximum and sustained response of the dP/dt (plotted as the unfilled triangles, labeled as "Average" in FIG. 2). This experimentally demonstrates the unexpected behavior elicited from specific ratio combinations. However, this method can predict these behaviors and is useful in determining other specific ratio combinations that produce a range of desirable responses in physiological systems.

EXAMPLE 3

Figure 3:
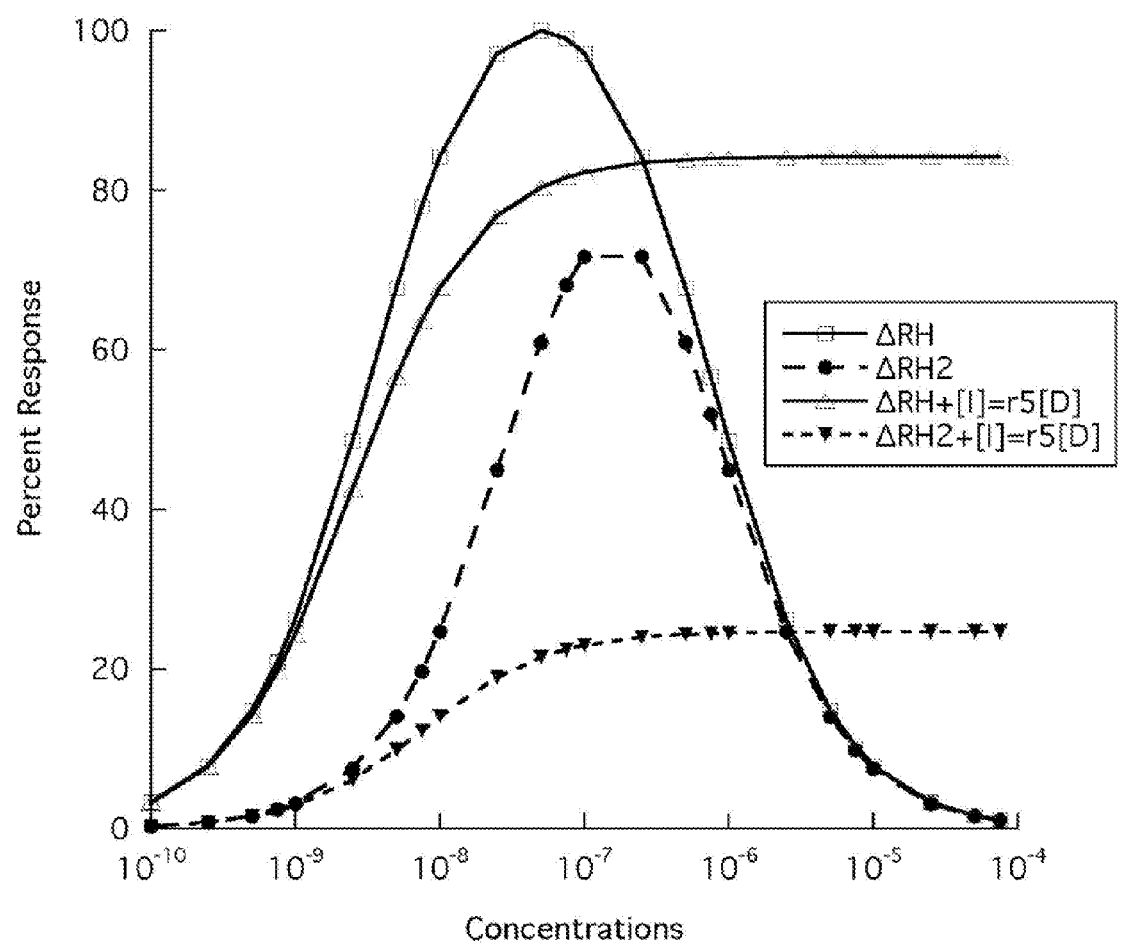
FIG. 3 is a graphical representation of the reduction in secondary responses achieved by using the method of the present invention to form a specific combination ratio.

In some dosing situations such as that depicted in FIG. 3, the primary response of the agonist drug, "D", produces the primary receptor response, which is plotted as the unfilled hollow squares for ΔRH. At a dose of $5 \times 10^{-8}$ [D], the response reaches its peak value of 100 percent. At the higher doses of [D], the response diminishes. This produces a characteristic "bell-shaped" curve. These "bell-shaped" curves very often reflect receptor responses, which have confounded the study of many pharmacological systems. This figure also shows a secondary receptor response, which is plotted as the filled circles (ΔRH2). Recent data reveal that many ligands differentially activate different signaling pathways mediated by differences in ligand-induced intermediate conformational states, as shown for the beta-2-adrenergic receptor, or other mechanisms that include the diversity of G proteins, multiple effector systems and signaling partners, and/or receptor oligomer formation. These phenomena have been recently termed "functional selectivity". However, some elements of these phenomena have also been previously labeled as "protean agonism".

Whether one uses the term "functional selectivity" or "protean agonism", some of these secondary receptor responses may produce the unwanted activation of intracellular pathways that lead to the side effects seen for many biological or pharmaceutical medicines and drugs. FIG. 3 demonstrates how we can control these unwanted effects. At the same dose that gave the maximal primary response to "D" ($5 \times 10^{-8}$ [D]), the secondary response (ΔRH2), reaches a value of about 61 percent response. Since the maximum value for the secondary response is a 72 percent response at a dose of about $1 \times 10^{-7}$ [D], the 61 percent response represents about 85% of the total maximum response of the secondary response. This may be within a range that produces significant side effects for patients receiving a near maximum dose of the drug, "D".

In order to prevent or ameliorate the occurrence of these side effects, we introduce a molecule that modulates the effects of "D". This molecule, is labeled "I" in FIG. 3. By introducing the molecule, "I", as a specific ratio in combination with "D", we produce a new combination product with better therapeutic properties compared to "D" alone. For example, if we compare the unfilled triangles (ΔRH+[I]=r5 [D]) in FIG. 3 with the solid black triangles (ΔRH2+[I]=r5 [D]), we find that the secondary response has decreased to about a 21 percent response at $5 \times 10^{-8}$ [D]. This represents a little more than a 65% decrease from the previously observed 61 percent response for the secondary response graphed above. This represents potentially significant gains in preventing the unwanted side effects as observed with "D" alone.

The combination (ΔRH+[I]=r5[D]) produces a 20 percent decrease in the maximum response (from 100% to 80%), but also decreases the secondary pathway by 65 percent (from 61% to 21%). This demonstrates the utility of this model to anticipate the beneficial effects of combining a biological or pharmaceutical medicine or drug, "D", with a modulating molecule, "I", into a specific ratio combination product (represented by ΔRH+[I]=r5[D] in the above graph and the specific ratio of the modulating molecule, "I", to the drug, "D", is [I]=r5[D] where "r" represents a specific ratio of [I] to [D]). This gives the proprietary amount of "I", to premix with the drug, "D" in order to produce a new and unique combination product. This new combination product would be expected to create fewer side effects with normal therapeutic usage.

EXAMPLE 4

Figure 4:
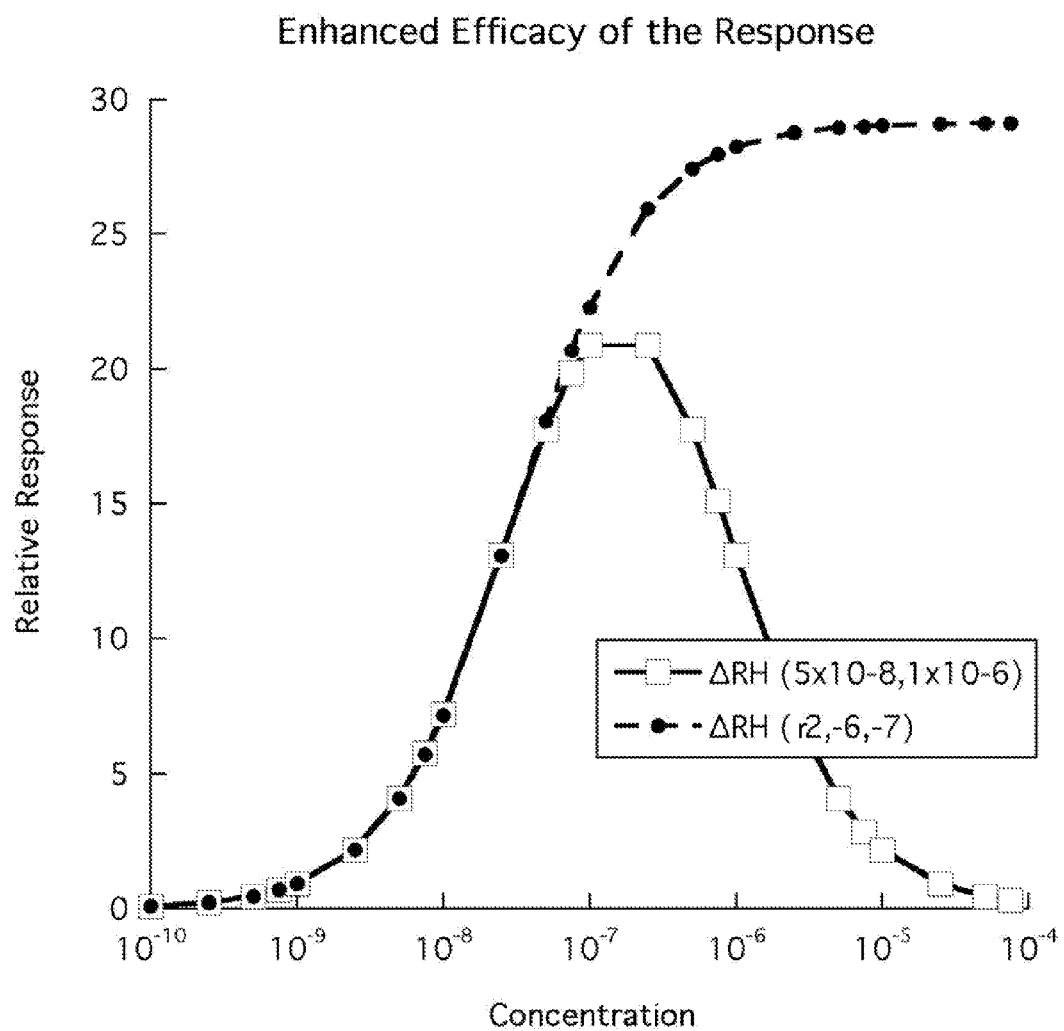
FIG. 4 is a graphical representation of the enhancement of the primary response by using the method of the present invention to form a specific combination ratio.

FIG. 4 shows the relative response of a single receptor stimulating drug shown as the unfilled white squares (ΔRH ($5 \times 10-8$, $1 \times 10-6$)) given at increasing doses, "[D]". In the figure, the expression for ΔRH ($5 \times 10-8$, $1 \times 10-6$) is shorthand for the two affinity constants $K_{DH}=5 \times 10^{-8}$, $K_{DL}=1 \times 10^{-6}$, which are used to model this response. The second response is the single drug combined with another molecule with the properties that its affinity constants are $K_{DH2}=1 \times 10^{-6}$, $K_{DL2}=1 \times 10^{-7}$ (ΔRH (f2,-6,-7)). The specific ratio of this second molecule to the first is given by "r2". This is the ratio that is necessary to produce the observed enhancement of the response to the drug alone (compare ΔRH ($5 \times 10-8$, $1 \times 10-6$) to ΔRH (r2,-6,-7) in the Figure). The addition of the second molecule in the specified ratio produces an enhanced response from about the middle portion of the response through the top of the curve for the single drug alone to a maximum response that is fifty percent greater than the maximum for the single drug alone. The second response also demonstrates a better therapeutic response that rises to a maximum and sustained response over the range of drug doses. This would be an additional therapeutic benefit from such specific ratio combinations.

Figure 5:
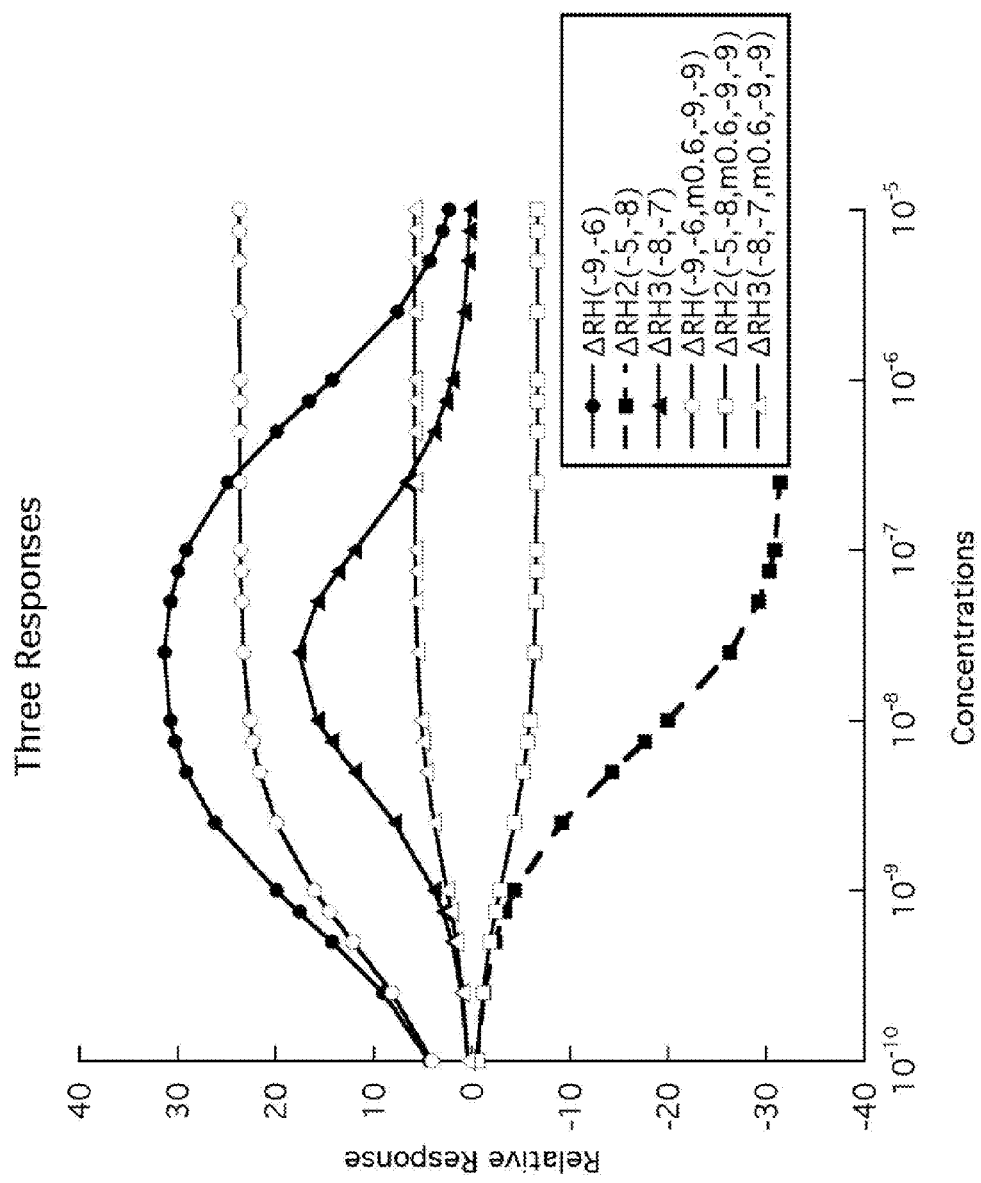
FIG. 5 depicts three responses to a single drug comparing the drug alone to a drug combination that minimizes the secondary responses.

FIG. 5 shows three relative responses produced from a single drug that may be labeled as a protean agonist or as functionally selective. For the single drug, these are plotted using the black filled shapes as ΔRH(- 9,-6), ΔRH2(-5,-8) and ΔRH3(-8,-7), where the numbers in parentheses represent the affinity constants (e.g., $10^{-8}$=-8) of the drug for each of the observed responses. If only the first response, labeled as ΔRH(- 9,-6) is the therapeutically desired response and the other two responses, labeled as ΔRH2 and ΔRH3, are the unwanted responses that may produce side effects, then in order to design a better therapeutic profile for this drug, we may want to limit those unwanted responses to under relative responses of ±10. It should be noted that ΔRH2 is an inverse agonist or negative antagonist response, which has been previously observed in experimental systems.

Once the responses of each molecule and of the combination(s) are modeled with the appropriate biophysical parameters then the model will show those regions that produce the desired inhibition of the unwanted responses while maintaining a sustained and near maximal desired response.

Figure 6:
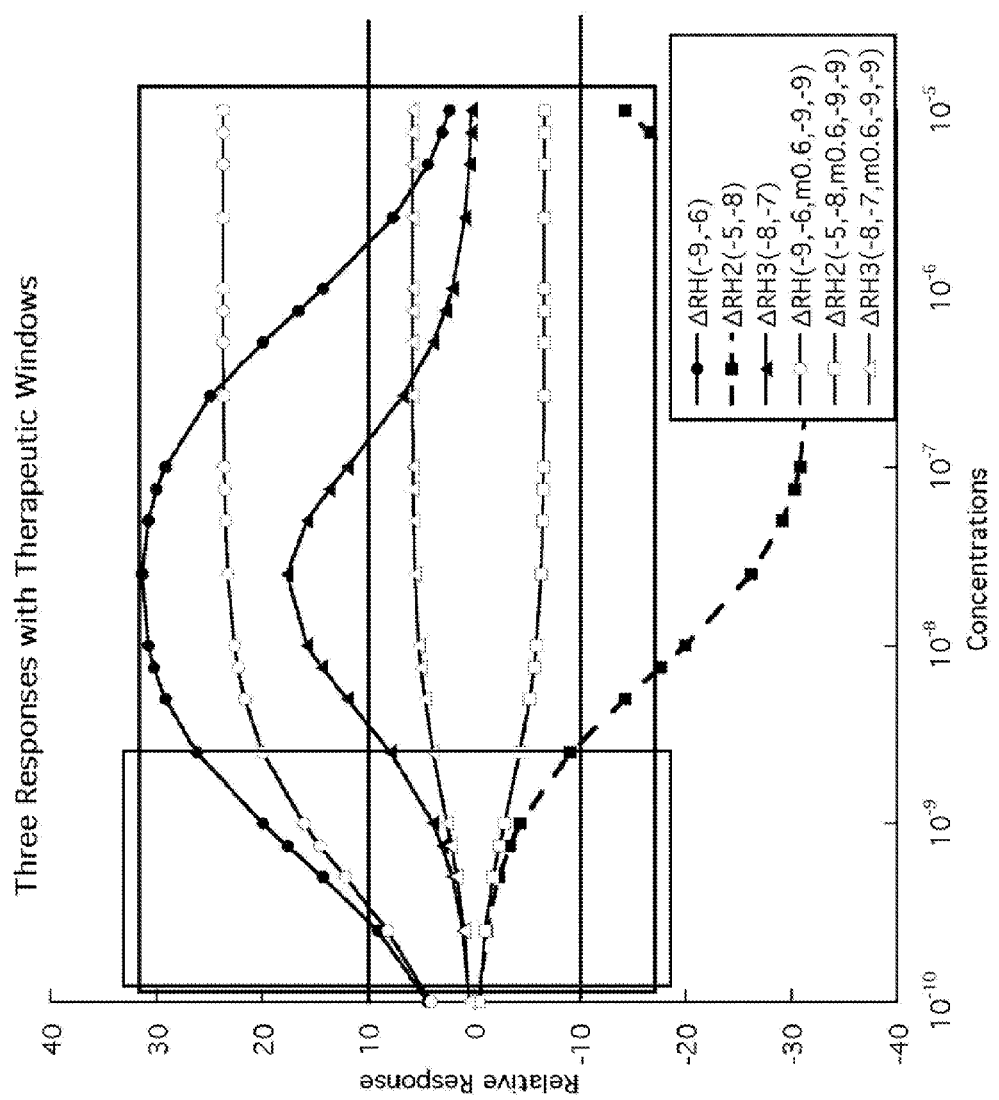
FIG. 6 depicts three responses to a single drug compared to a drug combination with their relative therapeutic windows.

FIG. 6 shows the difference in the therapeutic windows for the main response with and without the modulator combination (m0.6). The two horizontal lines at +10 and −10 represent the acceptable levels of the secondary responses, ΔRH2 and ΔRH3. If we wish to maintain the maximum for the primary response, ΔRH, at 20 or more and the levels of the secondary responses at plus or minus 10 or less, then for the single drug alone, shown by the filled black symbols, the therapeutic window is the smaller window to the left at about $2.5 \times 10^{-9}$ whereas for the drug combination the therapeutic window extends across the entire x-axis. This demonstrates how these specific ratio combinations can increase the safety and efficacy of drugs used alone.

Experimental examples of ligands showing different pharmacologic activities for various intracellular pathways have been previously observed. Such ligands can display full agonist activity for one pathway and partial agonist or antagonist or even inverse agonist activity for another intracellular pathway. The protean nature of these signaling molecules has demonstrated the potential for extraneous signaling in many clinically important drugs.

Figure 7:
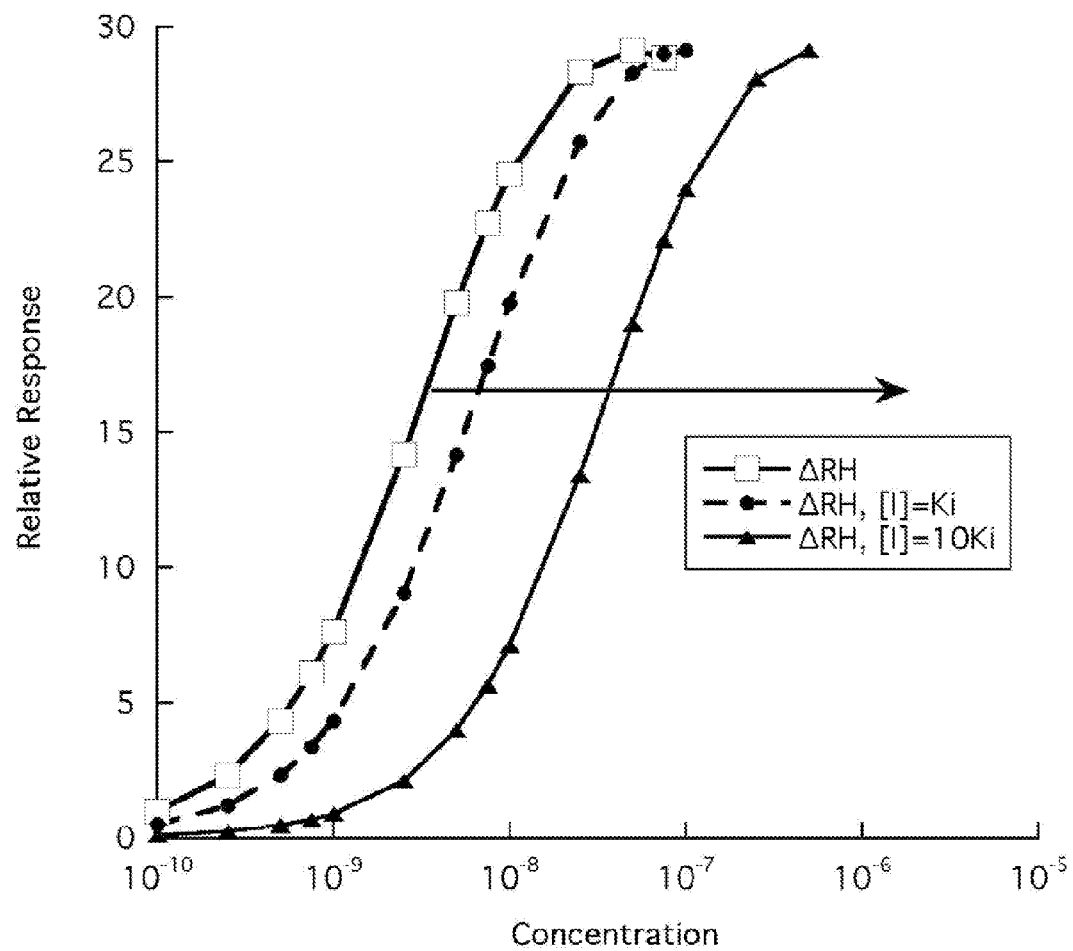
FIG. 7 demonstrates the classical shift to the right for a dose-response curve exposed to increasing fixed doses of an antagonist.

FIG. 7 shows the ability of the model embodied in the method of the present invention to depict the expected shift to the right of the dose-response curves with increasing doses of a competitive antagonist "I". As an example, some molecule, "I", may compete with "D" for each of the two states. If this competing molecule has equal or almost equal affinities for each of the two states, then this is seen as simple competitive inhibition, which shifts the dose-response curve in parallel to the right. In this model, this shift to the right obeys the Schild relationship, which is an important test for pharmacodynamic models. Alternatively, molecule "I" may have different affinities for each of the two receptor states. This may produce a different pattern for the inhibition as well as the phenomenon known as "inverse agonism" or "negative antagonism". These phenomena are produced if the molecule shows a higher affinity for the $R_L$ over the $R_H$ state.

Figure 8:
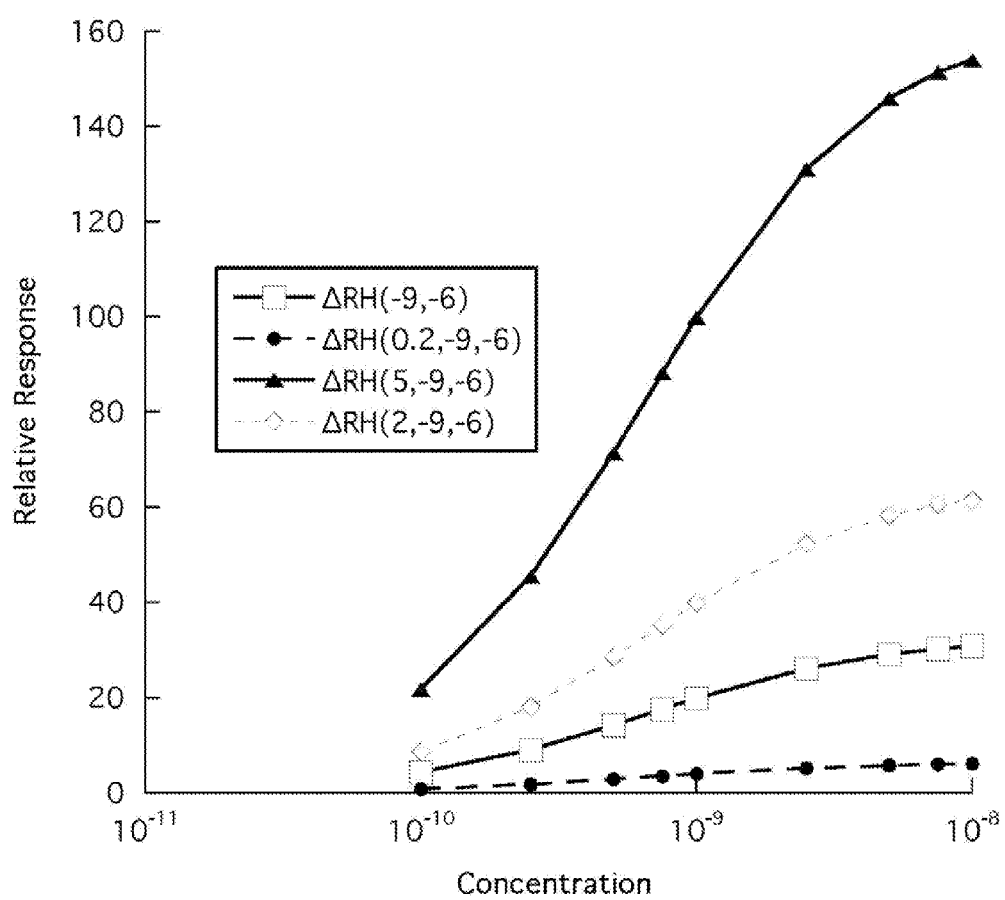
FIG. 8 demonstrates the decline in response to successive reductions in the active receptor number.

FIG. 8 shows the increase or decrease of receptor responses due to a modulator that acts to increase or decrease the active receptor number. This is another familiar phenomenon of drug-receptor pharmacology that demonstrates the validity and versatility of the biophysical model embodied in the method of the present invention.

The method of the present invention represents several advances that include: (1) a scientific method to determine the specific effects of combining drugs of differing efficacies and affinities with one another on the overall drug-receptor response; (2) a method to selectively modulate the receptor response to encompass any response from the full range of responses from inverse agonism to partial agonism to full agonism; (3) a scientific method to determine specific drug combinations that can modulate the receptor response to accomplish: (a) the enhancement of standard pharmacological or medical treatment with hormones, peptides or drugs; (b) the prevention or reduction of side effects such as desensitization, tachyphylaxis, tolerance, down-regulation, autoinhibition, fade, wearing-off, resistance, and/or subsensitivity; (c) the enhancement of the response to endogenously produced hormones and/or metabolites; (d) the enhancement of cross receptor modulation; and (e) the accurate titration of medically desired endpoints using drug combinations that can modulate the targeted receptor response. This method may be specifically applied to molecules and drugs generally classified as agonists, antagonists, partial agonists, inverse antagonists, negative agonists, partial inverse antagonists, partial negative agonists, partial inverse antagonists, partial negative agonists or neutral antagonists.

This more physiologically subjective and practical method, and the specific ratio compositions derived thereby, constitute effective and significant improvements to the known prior art. They are commended to the field consistent with the hereinafter appended claims.

What is claimed is:

1. A method for creating drug combinations that modulate at least one desired primary response of a cellular receptor and that prevent or reduce at least one undesired secondary response of the cellular receptor, said method comprising the steps of:
   selecting a first drug known for eliciting the at least one desired primary response;
   determining biophysical parameters of the first drug over a full range of dose-response curve of the at least one desired primary response;
   determining biophysical parameters of the first drug for the at least one undesired secondary response;
   determining a modulated primary response level that is below a theoretical maximal response level of the first drug;
   selecting a second drug or molecule which modulates the first drug response specific to the cellular receptor at or below the modulated primary response level;
   determining biophysical parameters of the second drug or molecule for the at least one desired primary response and the at least one undesired secondary response;
   determining an amount of the second drug or molecule that prevents or reduces the at least one undesired secondary response based at least in part upon the biophysical parameters of the first drug for the full dose-response curve of the at least one desired primary response, based at least in part upon the biophysical parameters of the first drug for the at least one undesired secondary response and at least in part upon the biophysical parameters of the second drug or molecule for the at least one desired primary response and the at least one undesired secondary response, wherein the amount of the second drug or molecule is determined to be a specific ratio of the second drug or molecule to the first drug; and
   combining a physical amount of the first drug and a physical amount of the second drug or molecule according to the specific ratio to form a composition that elicits the at least one desired primary response and prevents or reduces the at least one undesired secondary response.

2. The method of claim 1, wherein the following formula calculates the amount of the second drug or molecule that prevents or reduces the at least one undesired secondary response:

$$\Delta RH = \frac{[m_2 R_L][DR_H] - [m_1 R_H][DR_L]}{[m_1 R_H] + [DR_H] + [m_2 R_L] + [DR_L]}$$

where $R_H$ and $R_L$ represent, respectively, high affinity and low affinity states of the cellular receptor, D represents a concentration of a binding drug or ligand, $m_1$ and $m_2$ represent effects of one or more modulators and ΔRH represents a net change that occurs to an initial $[R_H]/[R_L]$ ratio.

3. The method of claim 1, wherein the following formula calculates the amount of the second drug or molecule that prevents or reduces the at least one undesired secondary response:

$$\Delta RH = \frac{m_1 R_H m_2 R_L(D)(m_4 K_{DL} - m_3 K_{DH})}{m_1 R_H(2D + m_3 K_{DH})(D + m_4 K_{DL}) + m_2 R_L(D + m_3 K_{DH})(2D + m_4 K_{DL})}$$

where $R_H$ and $R_L$ represent, respectively, high affinity and low affinity states of the cellular receptor, D represents a concentration of a binding drug or ligand, $K_{DH}$ and $K_{DL}$ represent, respectively, affinity constants that the binding drug or ligand has for $R_H$ and $R_L$, $m_1$, $m_2$, $m_3$ and $m_4$ represent effects of one or more modulators and $\Delta RH$ represents a net change that occurs to an initial $[R_H]/[R_L]$ ratio.

4. The method of claim 1, wherein at least one of the following formulae calculates the amount of the second drug or molecule that prevents or reduces the at least one undesired secondary response:

$$m=(1+([I])/K_i)$$

$$m=(1+(r[D])/K_i)$$

$$m=r[D]$$

$$m=r$$

where m represent an effect of a modulator, D represents a concentration of a binding drug or ligand, I represents a concentration of a modulating drug or molecule, $K_i$ represents an affinity constant of the modulating drug or molecule, and r represents a specific ratio of the modulating drug or molecule to the first binding drug or ligand.

5. The method of claim 1, wherein the at least one undesired secondary response comprises unwanted side effects of the first drug taken alone.

6. The method of claim 1, wherein the first drug is a biological or pharmaceutical medicine or drug.

7. The method of claim 1, wherein the biological parameters of the first drug for the full dose-response curve of the desired primary receptor response comprise high and low affinity binding constants of the first drug.

8. The method of claim 1, wherein the biological parameters of the first drug for the at least one undesired secondary receptor response comprise high and low affinity binding constants of the first drug.

9. The method of claim 1, wherein the second drug or molecule is selected from the group consisting of: competitive neutral antagonists, negative antagonists, partial agonists, inverse agonists and agonists.

10. The method of claim 1, wherein the biological parameters of the second drug or molecule for the at least one desired primary response and the at least one undesired secondary response comprise high and low affinity binding constants of the second drug.

11. The method of claim 1, wherein said step of selecting a first drug suitable for eliciting the at least one desired primary response comprises the step of selecting a first drug suitable for maximizing the at least one desired primary response.

12. The method of claim 1, wherein said step of selecting a first drug suitable for eliciting the at least one desired primary response comprises the step of selecting a first drug suitable for maintaining a sustained and therapeutically desirable primary response.

13. The method of claim 1, wherein the at least one undesired secondary response comprises at least one of the following: phosphorylation, dephosphorylation, methylation or demethylation of various intracellular proteins, recruitment of other unwanted intracellular pathways, and molecular recruitment or binding by modulating molecules.

14. The method of claim 13 wherein the modulating molecules are selected from the group consisting of histones, nitroso-compounds, arrestins, sulfhydryl-modulators and other intracellular modulators.

15. The method of claim 1 wherein the first drug comprises a protean agonist, and wherein the second drug or molecule is selected from the group consisting of antagonists, partial agonists, inverse agonists and negative antagonists.

16. The method of claim 1 wherein the first drug is selected from the group consisting of agonists, partial agonists, inverse agonists and negative antagonists.

17. A method for creating combinations of pharmaceuticals or other bioactive molecules and ligands to activate, modulate, prevent and/or diminish unwanted intracellular signaling pathways, said method comprising the steps of:
   determining biophysical parameters of a first drug for at least one desired primary response and at least one undesired secondary response;
   determining a modulated primary response level that is below a theoretical maximal response level of the first drug;
   selecting a second drug or molecule which modulates binding and/or function of the first drug at or below the modulated primary response level;
   determining biophysical parameters of the second drug or molecule for the at least one desired primary response and the at least one undesired secondary response;
   determining an amount of the second drug or molecule that prevents or reduces the at least one undesired secondary response based at least in part upon the biophysical parameters of the first drug for the at least one desired primary response and the at least one undesired secondary response and at least in part upon the biophysical parameters of the second drug or molecule for the at least one desired primary response and the at least one undesired secondary response, wherein the amount of the second drug or molecule is determined to be a specific ratio of the second drug or molecule to the first drug; and
   combining a physical amount of the first drug and a physical amount of the second drug or molecule according to the specific ratio to form a composition that elicits the at least one desired primary response and prevents or reduces the at least one undesired secondary response to a specified background level.

18. The method of claim 17, wherein the following formula calculates the amount of the second drug or molecule that prevents or reduces the at least one undesired secondary response:

$$\Delta RH = \frac{[m_2 R_L][DR_H] - [m_1 R_H][DR_L]}{[m_1 R_H] + [DR_H] + [m_2 R_L] + [DR_L]}$$

where $R_H$ and $R_L$ represent, respectively, high affinity and low affinity states of the cellular receptor, D represents a concentration of a binding drug or ligand, $m_1$ and $m_2$ represent effects of one or more modulators and $\Delta RH$ represents a net change that occurs to an initial $[R_H]/[R_L]$ ratio.

19. The method of claim 17, wherein the following formula calculates the amount of the second drug or molecule that prevents or reduces the at least one undesired secondary response:

$$\Delta RH = \frac{m_1 R_H m_2 R_L (D)(m_4 K_{DL} - m_3 K_{DH})}{m_1 R_H (2D + m_3 K_{DH})(D + m_4 K_{DL}) + m_2 R_L (D + m_3 K_{DH})(2D + m_4 K_{DL})}$$

where $R_H$ and $R_L$ represent, respectively, high affinity and low affinity states of the cellular receptor, D represents a concentration of a binding drug or ligand, $K_{DH}$ and $K_{DL}$ represent, respectively, affinity constants that the binding drug or ligand has for $R_H$ and $R_L$, $m_1$, $m_2$, $m_3$ and $m_4$ represent effects of one or more modulators and $\Delta RH$ represents a net change that occurs to an initial $[R_H]/[R_L]$ ratio.

20. The method of claim 17, wherein at least one of the following formulae calculates the amount of the second drug or molecule that prevents or reduces the at least one undesired secondary response:

$$m=(1+([I])/K_i)$$

$$m=(1+(r[D])/K_i)$$

$$m=r[D]$$

$$m=r$$

where m represent an effect of a modulator, D represents a concentration of a binding drug or ligand, I represents a concentration of a modulating drug or molecule, $K_i$ represents an affinity constant of the modulating drug or molecule, and r represents a specific ratio of the modulating drug or molecule to the first drug binding drug or ligand.

21. The method of claim 17, wherein the at least one undesired secondary response comprises unwanted side effects of the first drug taken alone.

22. The method of claim 17, wherein the first drug is a biological or pharmaceutical medicine or drug.

23. The method of claim 17, wherein the biological parameters of the first drug comprise high and low affinity binding constants of the first drug.

24. The method of claim 17, wherein the second drug or molecule is selected from the group consisting of: competitive neutral antagonists, negative antagonists, partial agonists, inverse agonists and agonists.

25. The method of claim 17, wherein the biological parameters of the second drug or molecule comprise high and low affinity binding constants of the second drug.

26. The method of claim 17, further comprising, before said step of determining biophysical parameters of a first drug, the step of selecting a first drug suitable for maximizing the at least one desired primary response.

27. The method of claim 17, further comprising, before said step of determining biophysical parameters of a first drug, the step of selecting a first drug suitable for maintaining a sustained and therapeutically desirable primary response.

28. The method of claim 17, wherein the at least one undesired secondary response comprises at least one of the following: phosphorylation, dephosphorylation, methylation or demethylation of various intracellular proteins, recruitment of other unwanted intracellular pathways, and molecular recruitment or binding by modulating molecules.

29. The method of claim 28 wherein the modulating molecules are selected from the group consisting of histones, nitroso-compounds, arrestins, sulfhydryl-modulators and other intracellular modulators.

30. The method of claim 17 wherein the first drug comprises a protean agonist, and wherein the second drug or molecule is selected from the group consisting of antagonists, partial agonists, inverse agonists and negative antagonists.

31. The method of claim 17 wherein the first drug is selected from the group consisting of agonists, partial agonists, inverse agonists and negative antagonists.

32. A method for creating drug combinations that modulate at least one desired primary response of a cellular receptor and that prevent or reduce at least one undesired secondary response of the cellular receptor, said method comprising the steps of:

selecting a first drug known for eliciting the at least one desired primary response, the first drug comprising a biological or pharmaceutical medicine or drug;

determining high and low affinity binding constants of the first drug over a full range of dose-response curve of the at least one desired primary response;

determining high and low affinity binding constants of the first drug for the at least one undesired secondary response;

determining a modulated primary response level that is below a theoretical maximal response level of the first drug;

selecting a second drug or molecule which modulates the first drug response specific to the cellular receptor at or below the modulated primary response level;

determining high and low affinity binding constants of the second drug or molecule for the at least one desired primary response and the at least one undesired secondary response;

determining an amount of the second drug or molecule that prevents or reduces the at least one undesired secondary response based at least in part upon the high and low affinity binding constants of the first drug for the full dose-response curve of the at least one desired primary response, based at least in part upon the high and low affinity binding constants of the first drug for the at least one undesired secondary response and based at least in part upon the high and low affinity binding constants of the second drug or molecule for the at least one desired primary response and the at least one undesired secondary response, wherein the amount of the second drug or molecule is determined to be a specific ratio of the second drug or molecule to the first drug; and combining a physical amount of the first drug and a physical amount of the second drug or molecule according to the specific ratio to form a composition that elicits the at least one desired primary response and prevents or reduces the at least one undesired secondary response.

33. The method of claim 32, wherein the following formula calculates the amount of the second drug or molecule that prevents or reduces the at least one undesired secondary response:

$$\Delta RH = \frac{[m_2 R_L][DR_H] - [m_1 R_H][DR_L]}{[m_1 R_H] + [DR_H] + [m_2 R_L] + [DR_L]}$$

where $R_H$ and $R_L$ represent, respectively, high affinity and low affinity states of the cellular receptor, D represents a concentration of a binding drug or ligand, $m_1$ and $m_2$ represent effects of one or more modulators and $\Delta RH$ represents a net change that occurs to an initial $[R_H]/[R_L]$ ratio.

34. The method of claim 32, wherein the following formula calculates the amount of the second drug or molecule that prevents or reduces the at least one undesired secondary response:

$$\Delta RH = \frac{m_1 R_H m_2 R_L (D)(m_4 K_{DL} - m_3 K_{DH})}{m_1 R_H (2D + m_3 K_{DH})(D + m_4 K_{DL}) + m_2 R_L (D + m_3 K_{DH})(2D + m_4 K_{DL})}$$

where $R_H$ and $R_L$ represent, respectively, high affinity and low affinity states of the cellular receptor, D represents a concentration of a binding drug or ligand, $K_{DH}$ and $K_{DL}$ represent, respectively, affinity constants that the binding drug or ligand has for $R_H$ and $R_L$, $m_1$, $m_2$, $m_3$ and $m_4$ represent effects of one or more modulators and $\Delta RH$ represents a net change that occurs to an initial $[R_H]/[R_L]$ ratio.

35. The method of claim 32, wherein at least one of the following formulae calculates the amount of the second drug or molecule that prevents or reduces the at least one undesired secondary response:

$m = (1+([I])/K_i)$ $m = (1+(r[D])/K_i)$ $m = r[D]$ $m = r$ where m represent an effect of a modulator, D represents a concentration of a binding drug or ligand, I represents a concentration of a modulating drug or molecule, $K_i$ represents an affinity constant of the modulating drug or molecule, and r represents a specific ratio of the modulating drug or molecule to the first drug binding drug or ligand.

\* \* \* \* \*